(12) United States Patent
Porterfield et al.

(10) Patent No.: US 8,882,977 B2
(45) Date of Patent: Nov. 11, 2014

(54) MICROBIOSENSORS BASED ON DNA MODIFIED SINGLE-WALLED CARBON NANOTUBE AND PT BLACK NANOCOMPOSITES

(75) Inventors: D. Marshall Porterfield, West Lafayette, IN (US); Tae-Gon Cha, West Lafayette, IN (US); Jong Hyun Choi, West Lafayette, IN (US); Jonathan C. Claussen, Lafayette, IN (US); Alfred R. Diggs, Chicago, IL (US); Jin Shi, San Diego, CA (US)

(73) Assignee: Purdue Research Foundation, West Lafayette, IN (US)

( * ) Notice: Subject to any disclaimer, the term of this patent is extended or adjusted under 35 U.S.C. 154(b) by 69 days.

(21) Appl. No.: 13/620,554

(22) Filed: Sep. 14, 2012

(65) Prior Publication Data

US 2013/0105328 A1     May 2, 2013

Related U.S. Application Data

(60) Provisional application No. 61/534,658, filed on Sep. 14, 2011.

(51) Int. Cl.
| | |
|---|---|
| *G01N 27/327* | (2006.01) |
| *C12Q 1/68* | (2006.01) |
| *C12Q 1/00* | (2006.01) |
| *B82Y 15/00* | (2011.01) |
| *B82Y 5/00* | (2011.01) |

(52) U.S. Cl.
CPC .............. *C12Q 1/001* (2013.01); *G01N 27/327* (2013.01); *C12Q 1/68* (2013.01); *B82Y 15/00* (2013.01); *B82Y 5/00* (2013.01); *C12Q 1/006* (2013.01); *Y10S 977/892* (2013.01); *Y10S 977/904* (2013.01); *Y10S 977/75* (2013.01)
USPC ................... 204/403.01; 205/109; 205/777.5; 435/287.1; 422/68.1; 422/82.01; 977/892; 977/904; 977/750; 156/242

(58) Field of Classification Search
USPC ............. 204/403.01–403.15; 205/109, 777.5; 422/68.1, 82.01; 435/287.1; 977/750, 977/892, 904
See application file for complete search history.

(56) References Cited

U.S. PATENT DOCUMENTS

| | | | |
|---|---|---|---|
| 7,939,734 B1 * | 5/2011 | Li et al. ........................... 435/6.1 |
| 2002/0034762 A1 * | 3/2002 | Muller et al. ...................... 435/6 |
| 2002/0128546 A1 * | 9/2002 | Silver ............................ 600/365 |
| 2006/0014155 A1 * | 1/2006 | Hamers et al. ..................... 435/6 |
| 2007/0233217 A1 * | 10/2007 | Yang et al. ..................... 607/126 |
| 2008/0262330 A1 * | 10/2008 | Reynolds et al. ............. 600/347 |

OTHER PUBLICATIONS

Shi et al., "A comparative study of enzyme immobilization strategies for multi-walled carbon nanotube glucose biosensors," Nanotechnology 22 (2011), 10 pp.

\* cited by examiner

*Primary Examiner* — Jennifer Dieterle
(74) *Attorney, Agent, or Firm* — John V. Daniluck; Bingham Greenebaum Doll LLP

(57) ABSTRACT

Glucose and ATP biosensors have important applications in diagnostics and research. Combining single-walled carbon nanotubes (SWCNTs) with Pt nanoparticles can significantly enhance the performance of electrochemical biosensors. This disclosure illustrates the use of single-stranded DNA (ssDNA) to modify SWCNTs to increase SWCNT solubility in water. Multiple embodiments with this configuration allows for exploration of new schemes of combining ssDNASWCNT and Pt black in aqueous media systems. These embodiments resulted in a nanocomposite with enhanced biosensor performance. The ssDNA-SWCNT/Pt black nanocomposite constructed by a layered scheme proved most effective in terms of biosensor activity. The key feature of this structure and method of use is the exploitation of ssDNASWCNTs as molecular templates for Pt black electrodeposition. Glucose and ATP microbiosensors fabricated utilizing this structure and method of use exhibited high sensitivity, wide linear range and low limit of detection.

20 Claims, 8 Drawing Sheets

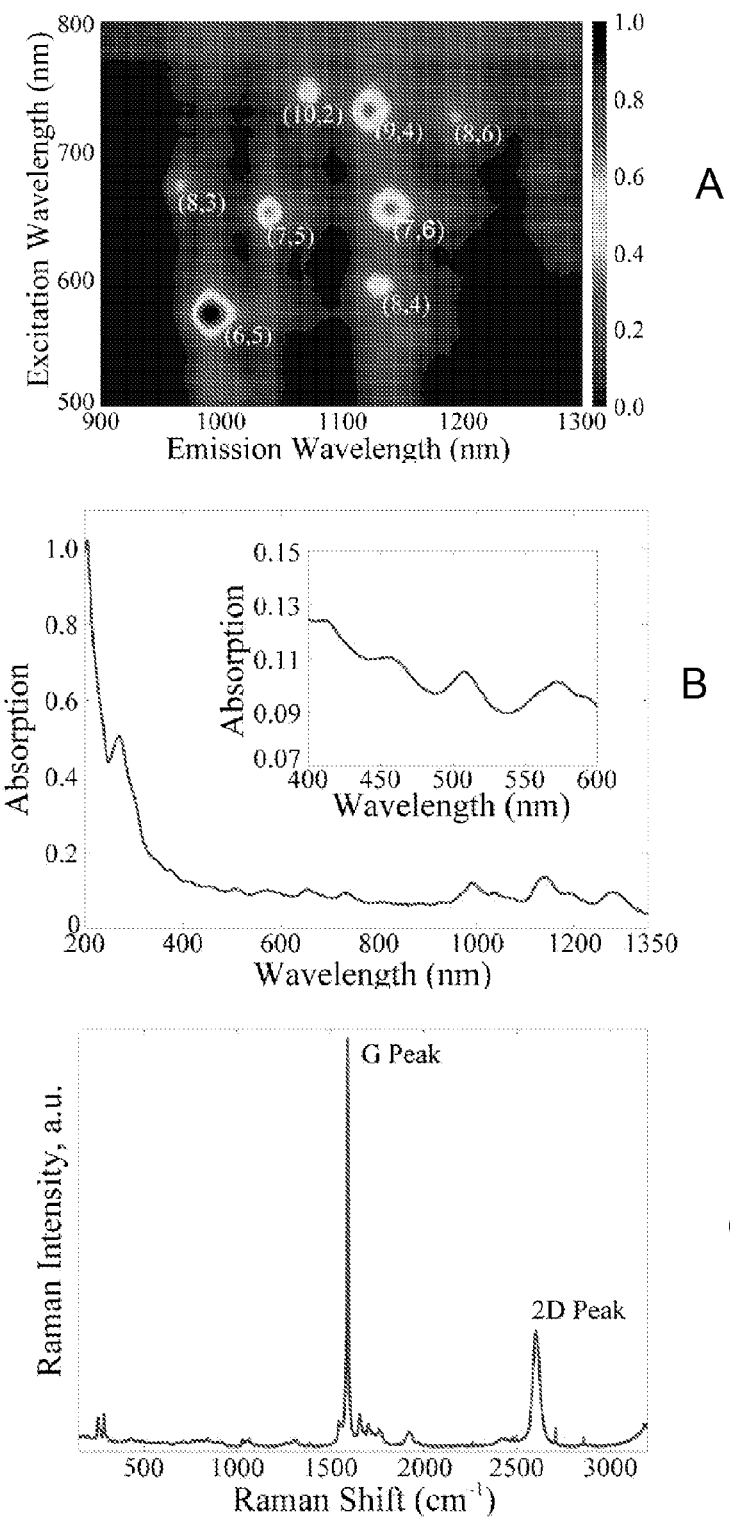
FIG. 1A, B, C

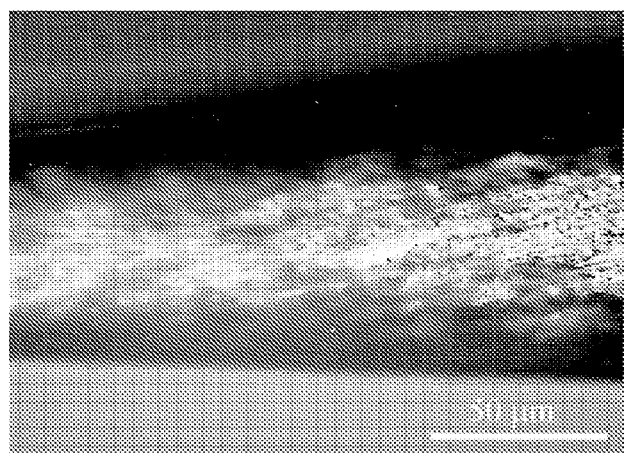
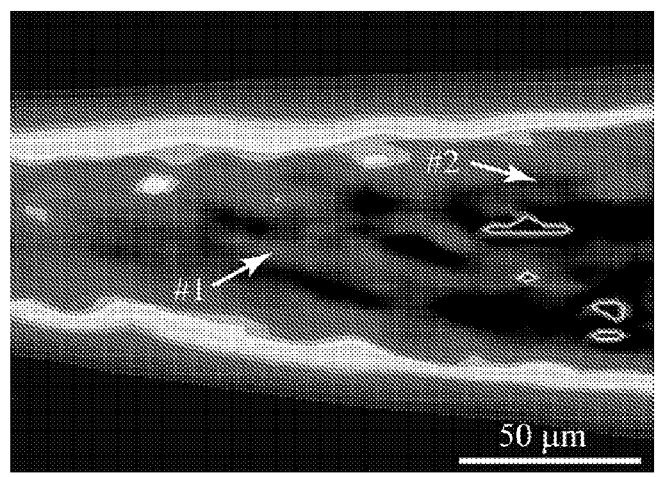
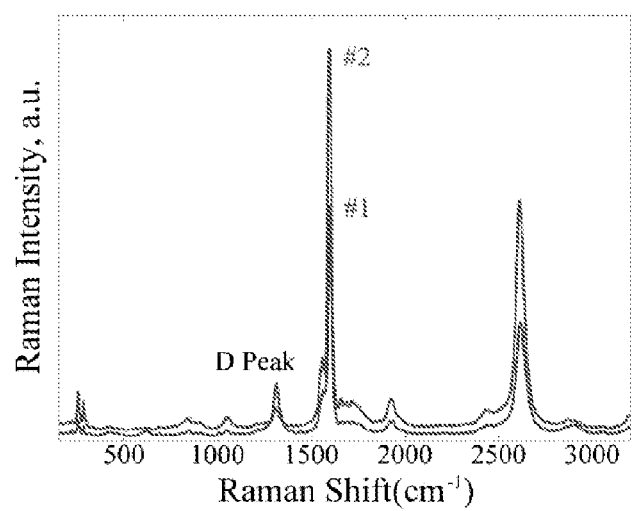
FIG. 1D, E, F

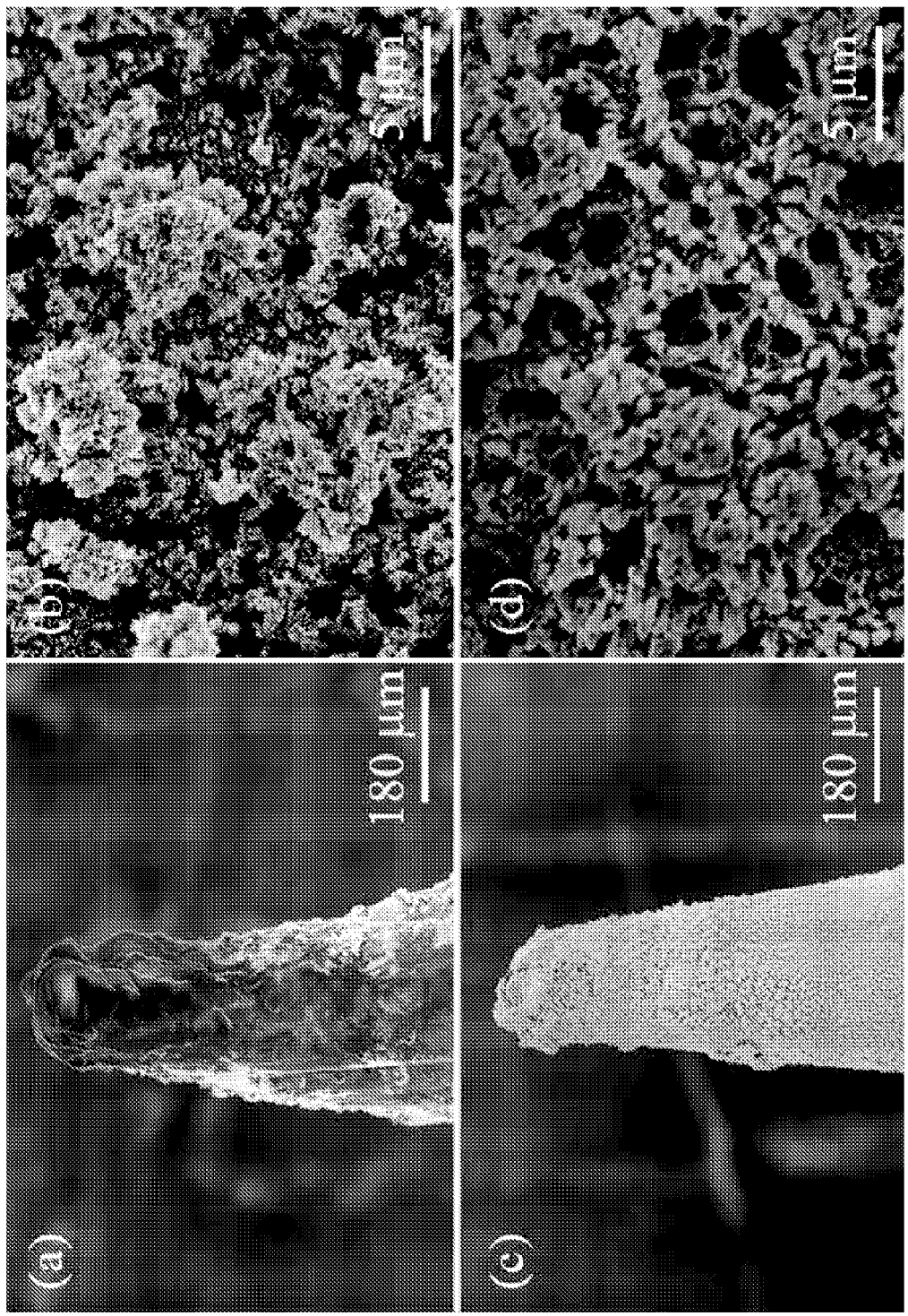
FIG. 2(a), (b), (c), (d)

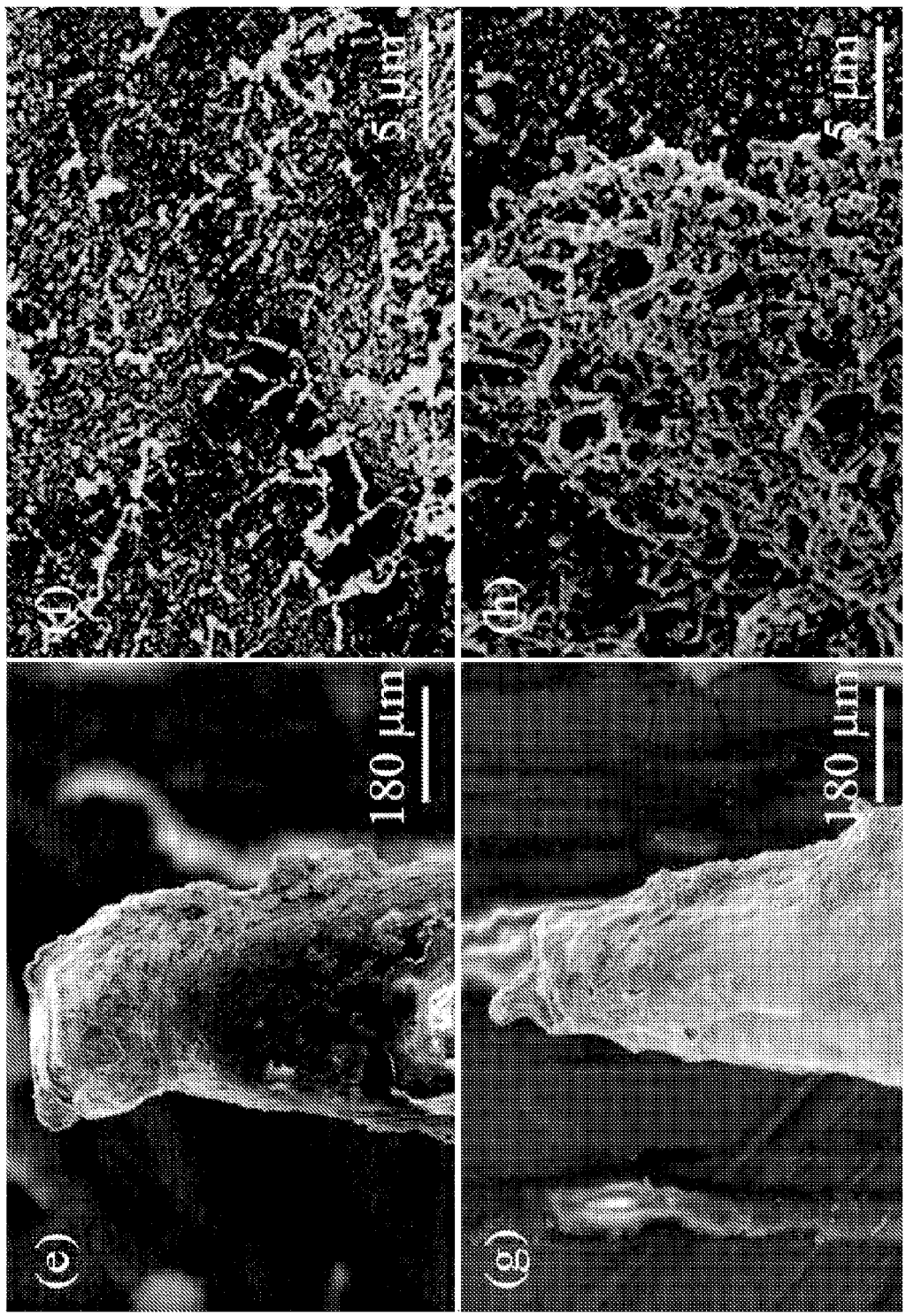
FIG. 2(e), (f), (g), (h)

MICROBIOSENSORS BASED ON DNA MODIFIED SINGLE-WALLED CARBON NANOTUBE AND PT BLACK NANOCOMPOSITES

CROSS REFERENCE TO RELATED APPLICATION

This application claims the benefit of U.S. Provisional Application No. 61/534,658, filed Sep. 14, 2011, the disclosure of which is expressly incorporated by reference.

FIELD

This disclosure relates to use of biosensors, specifically a biosensor including single strand DNA immobilized with single wall carbon nanotubes with Pt black nanocomposite structure constructed by a layered scheme to increase biosensor activity.

BACKGROUND

Glucose is one of the most important biochemical substrates for cellular catabolism. Glucose biosensors measure glucose based on enzymatic recognition of glucose by glucose oxidase (GOx) and have been widely used in diagnostics (e.g. diabetes monitoring) and research (e.g. β cell physiology study).

ATP is the fundamental unit of currency in cellular energetics, and also an important extracellular messenger in eukaryotic systems. Biosensors have been developed to measure ATP which show great advantages over conventional techniques. The main difference between ATP biosensors and glucose biosensors is that ATP biosensing is based on a multi-enzyme approach to convert ATP into an electro-oxidative species. ATP can be measured by combining hexokinase and GOx. One major drawback with this scheme is that the linear range is up to 200 nM, which is lower than human plasma ATP concentration (up to 11 μM) and limits its physiological applications. A second measurement scheme using a two enzyme system of glycerol kinase (GK) and glycerol-3-phosphate oxidase (G3POx) is adopted in this study, because it has been reported to have a wider linear range (up to 50 μM) compared with the first scheme, which is important for physiological applications. Additionally, it has been applied in vivo to study ATP signaling during spinal motor activity. Although ATP biosensors possess the potential to be an extremely useful tool for cell physiology, reports on electrochemical ATP biosensors are still quite limited.

Electrochemical biosensors are highly effective in monitoring biomolecule concentrations due to the high sensitivity, real-time monitoring capabilities and low cost. This contrasts with conventional measurement techniques including radioisotope tracing, NMR spectroscopy, and microfluorometry assays, which are complex and expensive but also are severely limited in terms of spatial and temporal resolution. Nanomaterials with good biocompatibility and electrocatalytic activities have received a lot of attention in terms of biosensing performance. However, biosensors based on conventional materials are constrained in terms of total sensitivity, which in turn limits the potential for miniaturization. This is due to restrictions in mass transport, enzyme loading, and electrochemical coupling. These sensitivity issues not impact the limit of detection, but also the signal-to-noise ratio in measuring very small changes in concentration over time. These parameters are key to exploring important physiological phenomena including β cell glucose consumption during insulin secretion.

Carbon nanotubes (CNT) and metal nanomaterials are the most commonly used nanomaterials in biosensor construction. CNTs are an allotrope of carbon. The carbon atoms at tube ends or at tube defect sites possess the catalytic capability for electrochemical reactions. The major obstacle for CNT immobilization is the fact that CNTs are minimally soluble in aqueous media due to van der Waals aggregation. Abrasive immobilization, CNT suspending polymers, linking agents and chemical vapor deposition (CVD) are the most successful current approaches for CNT preparation. Apart from these approaches, biochemical modification of CNTs (e.g. glucosamine and single-stranded DNA (ssDNA)) significantly increases the solubility in water, thus opening up technical approaches for CNTs that can be mediated in aqueous media. This greatly enhances the application of CNTs for microbiosensor applications. There are problems associated with current approaches. Abrasive immobilization is not possible with microscale devices. The main problem with polymers and linking agent immobilization is that residual materials remain on the biosensor after CNT immobilization, which limits mass analyte transport and sensor sensitivity. By adopting aqueous media based modifier approaches there is potential to apply CNT nanomaterials to microbiosensors using technical approaches that will preserve the effective surface area. Compared with other approaches, CVD is relatively complicated and expensive, ssDNA modification is much easier and cheaper. ssDNA modified single-walled CNTs have been demonstrated to dramatically increase the electroanalytical current output, while decreasing the redox overpotential for electrochemistry, and has been used as a catalyst for redox reactions. This is explained by virtue of a systematic change in SWCNT valence energy levels due to DNA wrapping. Sensors incorporating ssDNA-SWCNT without enzymes exhibited increased sensitivity towards the electrochemical measurement of dopamine via direct oxidation.

Platinum black (Pt black) is a metal formed by electrodepositing amorphous clusters of Pt nano-particles. Pt black has been used to enhance biosensor sensitivity due to the catalytic activity of Pt nano-particles, and the ease of attaching enzymes to Pt via cross-linking agents (e.g. glutaraldehyde). Previous studies that combine both CNTs and Pt nanomaterials have exhibited improved performance than using either material alone.

SUMMARY

The present disclosure includes a biosensor comprising an electrode including single strand DNA immobilized with single wall carbon nanotubes on the electrode utilizing a scheme for electrodeposition of Pt black on the electrode for aqueous media based analysis.

The present disclosure also includes a method of manufacturing a biosensor, the method comprising the steps of providing an electrode for use with aqueous media, attaching single strand DNA, single walled carbon nanotubes and Pt black on the electrode, and cross linking an enzyme to the Pt black.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 1(a) illustrates a photoluminescence excitation profile of ssDNA-SWCNTs showing distinct near-IR (NIR) fluorescence. FIG. 1(b) illustrates the corresponding absorption spectrum of the ssDNA-SWCNTs of FIG. 1(a). Inset shows a fraction of metallic species. FIG. 1(c) illustrates the Raman spectrum of ssDNA-SWCNTs with a HeNe laser excitation at 633 nm. FIG. 1(d) illustrates a visible image after deposition of ssDNA-SWCNTs on an electrode. FIG. 1(e) illustrates a reconstructed Raman image using G band intensity (v=~1590 $cm^{-1}$) of ssDNA-SWCNTs deposited on the electrode. FIG. 1(f) illustrates the Raman spectra detected at marked positions #1 and #2 from FIG. 1(e).

FIG. 2(a) illustrates a SEM image of micro electrodes modified with Pt black. FIG. 2(b) illustrates a magnified image of FIG. 2(a). FIG. 2(c) illustrates a layered scheme. FIG. 2(d) illustrates a magnified image of FIG. 2(c). FIG. 2(e) illustrates a co-deposition scheme. FIG. 2(f) illustrates a magnified image of FIG. 2(e). FIG. 2(g) illustrates a combination of the layered and the co-deposition schemes. FIG. 2(h) illustrates a magnified image of FIG. 2(g).

Figure 3:
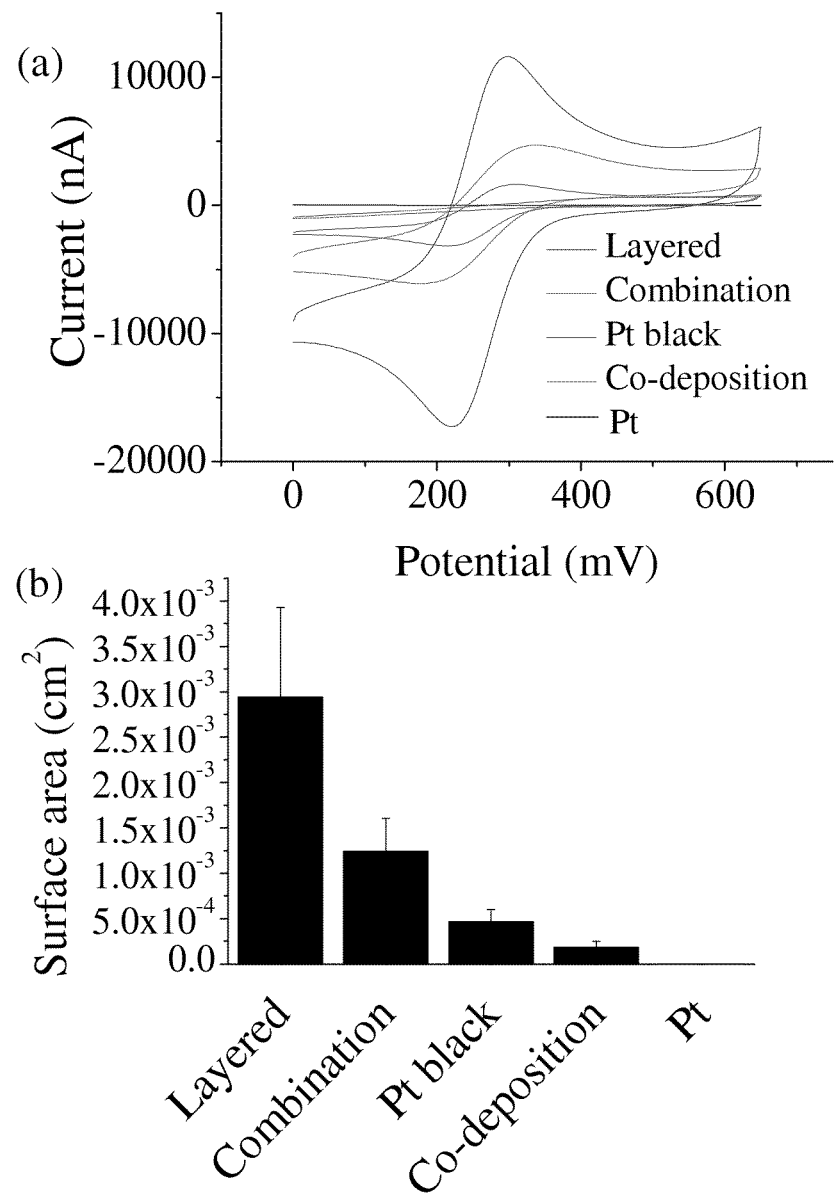
FIG. 3(a) illustrates Cyclic Voltametry (CV) in $Fe(CN)_6^{3-}$ for a bare electrode and electrodes modified with Pt black, layered, co-deposition and combination schemes.
FIG. 3(b) illustrates a histogram showing the average electroactive surface area of micro electrodes based on the different schemes shown in FIG. 3a (error bars represent standard error of the mean (n=3)).

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings. For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates. At least one embodiment of the present invention will be described and shown, and this application may show and/or describe other embodiments of the present invention. It is understood that any reference to "the invention" is a reference to an embodiment of a family of inventions, with no single embodiment including an apparatus, process, or composition that should be included in all embodiments, unless otherwise stated. Further, although there may be discussion with regards to "advantages" provided by some embodiments of the present invention, it is understood that yet other embodiments may not include those same advantages, or may include yet different advantages. Any advantages described herein are not to be construed as limiting to any of the claims.

Although various specific quantities (spatial dimensions, temperatures, pressures, times, force, resistance, current, voltage, concentrations, wavelengths, frequencies, heat transfer coefficients, dimensionless parameters, etc.) may be stated herein, such specific quantities are presented as examples, and further, unless otherwise noted, are approximate values, and should be considered as if the word "about" prefaced each quantity. Further, with discussion pertaining to a specific composition of matter, that description is by example, and does not limit the applicability of other species of that composition, nor does it limit the applicability of other compositions unrelated to the cited composition.

Apart from these approaches, biochemical modification of CNTs (e.g. glucosamine and single-stranded DNA (ssDNA)) significantly increases the solubility in water, thus opening up technical approaches for CNTs that can be mediated in aqueous media. This greatly enhances the application of CNTs for microbiosensor applications.

This disclosure explores possible ways of combining ssDNA-SWCNT and enzyme based approaches utilizing Pt black for micro biosensor enhancement. Microelectrodes modified with different schemes are characterized with SEM, cyclic voltammetry and DC potential amperometry. For different schemes, effective surface area and electrocatalytic activities in terms of amperometric sensitivity to $H_2O_2$ are studied and compared. By attaching the de facto enzyme GOx, and the two enzyme system of GK and G3POx to modified electrodes, single-enzyme and multi-enzyme micro biosensors are constructed and compared to determine the most effective scheme for both glucose and ATP microbiosensors. Major parameters for biosensors based on the most effective scheme are characterized to demonstrate that they can be used in a wide variety of physiological sensing applications. It is also envisioned that other single enzyme approaches or other multi enzyme approaches, such as hexohikanse and GOx, would work for micro biosensor enhancement.

Considering the advantages of ssDNA-SWCNT over existing CNT immobilization approaches, incorporating ssDNA-SWCNTs with Pt black may greatly enhance biosensing. Since ssDNA-SWCNTs are conductive/semiconductive, they can be used as molecular templates for Pt black electrodeposition, and as electrical contacts between Pt black and electrode. Thus, possible aqueous media based schemes of combining ssDNA-SWCNT and Pt black are: 1. immobilize ssDNA-SWCNT on the micro electrode by cast-and-dry, and electrodeposit Pt black over ssDNA-SWCNT ("layered" scheme), 2. mix ssDNA-SWCNT with the electrodeposition media for Pt black (chloroplatinic acid/lead acetate solution), and co-electrodeposit both materials ("co-deposition" scheme) and 3. immobilize ssDNA-SWCNT by cast-and-dry, mix ssDNA-SWCNT with the electrodeposition media, and co-electrodeposit both materials, which essentially combines the layered scheme and the co-deposition scheme ("combination" scheme).

Construction of Microbiosensors. All micro sensors were constructed on a Pt/Ir microelectrode (PI20033.0A10, 51 mm length, 0.256 mm shaft diameter, 1-2 μm tip diameter). The design schemes that used nanomaterials are:

Pt black scheme: The microelectrode was connected to a potentiostat (cathode) against a bare Pt wire (0.5 mm in diameter; Alfa Aesar, Ward Hill, Mass.) (anode). Pt black was electrodeposited using a potentiostat (Applicable Electronics) in a solution of 0.36% chloroplatinic acid and 0.0005% lead acetate (10V for 1 minute).

Layered scheme: 2 μl ssDNA-SWCNT (69.19 mg/L) was cast on the microelectrode and air-dried for 30 min. Pt black was then electrodeposited following the Pt black scheme protocol for electrodeposition.

Co-deposition scheme: Pt black was electrodeposited following the protocol for the Pt black scheme except that the solution contained 69.19 mg/L ssDNA-SWCNT in addition to 0.36% chloroplatinic acid and 0.0005% lead acetate.

Combination scheme: 2 μl ssDNA-SWCNT (69.19 mg/L) was cast on the microelectrode and air-dried for 30 min. Pt black was then electrodeposited following the protocol for the co-deposition scheme. Combination scheme here means combining the layered and the co-deposition schemes.

Glucose biosensor: 60 μl 50 mg GOx/ml Phosphate Buffered Saline (PBS) was mixed with 40 μl 25 mg/ml Bovine Serum Albumin (BSA)/ml PBS and 20 μl 2.5% glutaraldehyde. 2 μl mixture was cast on the micro electrode and air-dried for 30 min.

ATP biosensor: 8 μl 60 mg glycerol-3-phosphate oxidase/ml Tris-HCl was mixed with 8 μl 60 mg glycerol kinase/ml Tris-HCl, 8 μl 1.6 M glycerol and 8 μl 2.5% glutaraldehyde. 2 μl mixture was cast on the micro electrode and air-dried for 30 min.

Chemicals and Reagents. All solutions, if not specified, were prepared in deionized water (DI) of resistivity 18.2 MΩ cm (Milli Q). Glucose oxidase (E.C.1.1.3.4, 100,000-250,000 units/g, from *Aspergillus niger*), D-Glucose, glycerol kinase (E.C.2.7.1.30, 25-75 units/mg, from *Cellulomonas* sp), glycerol 3-phosphate oxidase (E.C.1.1.3.21, ≥10 units/mg solid, from *Streptococcus thermophilus*), adenosine-5-phosphate (disodium salt hydrate), glycerol (99%), potassium chloride (KCl, 99%), potassium ferricyanide ($K_3Fe(CN)_6$), chloroplatinic acid solution (8% wt/wt), lead acetate (reagent grade, 95%), sodium chloride (NaCl), magnesium chloride (≥99%), Tris(hydroxymethyl)aminomethane, hydrochloric acid (HCl) (≥30%), bovine serum albumin and glutaraldehyde (Grade II, 25% Aqueous Solution) were purchased from Sigma-Aldrich (St. Louis, Mo.). Sodium phosphate ($Na_2HPO_4 \cdot 7H_2O$) and potassium phosphate ($KH_2PO_4$, monobasic) were purchased from Fisher chemicals (Pittsburg, Pa.). PBS solution (0.01M) was prepared by dissolving 8.0 g NaCl, 1.2 g $Na_2HPO_4$, 0.2 g KCl and 0.2 g $KH_2PO_4$ in 1.0 L DI. Tris-HCl buffer was prepared by dissolving 1 M Tris(hydroxymethyl)aminomethane and adjusting the pH to 8.3 with HCl. Bulmer's buffer was prepared by dissolving 100 mM NaCl, 2 mM glycerol and 1 mM $MgCl_2$ in 2 mM $Na_2HPO_4$ buffer.

ssDNA-SWCNT Sample Preparation. HiPco SWCNTs (Unidym, Sunnyvale, Calif.) were dispersed in aqueous solution using single-stranded, 30 base-long poly T oligonucleotides (Integrated DNA Technologies, Coralville, Iowa). This disclosure specifies single-stranded, 30 base-long poly T oligonucleotides due to its ease of synthesis and its limited interaction with other compounds. It is envisioned that any form of DNA may be used including any double stranded or single stranded forms. Briefly, raw nanotube powder with DNA in solution was bath-sonicated for 1 hour and centrifuged at 15,000 rpm for 150 min. After centrifugation, the supernatant was carefully decanted to separately obtain DNA-coated SWCNTs from denser catalyst particles, bundles, and impurities. The concentration of SWCNTs was estimated to be approximately 23.8 mg/L.

Sensor Calibration. DC potential amperometry was conducted with a 3 electrode electrochemical (C-3) cell stand (BASi, West Lafayette, Ind.) at a working potential of +500 mV versus a Ag/AgCl reference electrode with a sampling rate of 1 kHz following previous disclosures. Reference electrodes (Ag/AgCl) and auxiliary electrodes were purchased from BASi. Amperometric sensitivity towards glucose was determined by measuring current at a constant working potential while sequentially adding glucose to mixed solutions (all solutions stirred at 300 rpm). Following each glucose addition, measured current signal was allowed to reach steady state (defined as less than a 3% fluctuation for 10 sec). Average current values represented the arithmetic mean of observed current (n=10,000 data points). Response time ($t_{95}$) was calculated as the time for the sensor to reach 95% of its maximum amperometric response following addition of 100 μM glucose. The same calibration protocol applied to ATP except that 3 mM glycerol was added into the cell before test because glycerol was required in the reaction cascade that measured ATP. Cyclic voltammetry (CV) was performed with a 3 electrode electrochemical (C-3) cell stand (BASi, West Lafayette, Ind.) in 4 mM $Fe(CN)_6^{3-}$/1 M $KNO_3$. A sweep range of 0 to +650 mV was used with a 10 second quiet time.

Optical Measurement. The excitation and emission spectra of DNA-coated SWCNTs were measured with Horiba Jobin Yvon spectrofluorometer with a $N_2$-cooled InGaAs detector (Edison, N.J.). The spectral resolutions in excitation and emission measurements were 4 nm and 3 nm, respectively. The optical absorption spectrum was measured by a Perkin Elmer Lambda 950 spectrophotometer (Waltham, Mass.). The Raman spectra were recorded using a Renishaw inVia Raman microscope with 633 nm excitation.

FESEM. All field emission scanning electron microscopy (FESEM) biosensor images were obtained using a Hitachi S-4800 microscope with a power setting of 5.0 kV and magnification settings of 3.5 k and 25 k (no additional preprocessing).

Optical Characterization and SEM. SWCNTs dispersed in aqueous solution using 30 base-long poly T DNA (ssDNA-SWCNT) showed discrete optical transitions at characteristic wavelengths ranging from visible to near-infrared. The signatures of optical absorption in the visible and photoluminescence in the near-infrared were shown in FIG. 1a, and assigned to specific nanotube species based upon chiral vectors, (n, m), which indicated the diameter and chirality of each nanotube. The nucleobases of the oligonucleotide strands non-covalently interacted with the graphitic lattice of nanotubes via π-π stacking, while negatively charged DNA backbone rendered ssDNA-SWCNT hybrids soluble in aqueous solution via entropic repulsion. Typical carbon nanotube synthesis methods produced a mixture of semiconducting and metallic species, and the fraction varied depending on synthesis conditions.

This disclosure utilized carbon nanotubes grown by the high-pressure CO disproportionation method or the so-called HiPco method, which typically included approximately two-thirds of semiconductors and a third of metallic species. These carbon nanotube mixtures have been demonstrated to be electrochemically active materials. The photoluminescence excitation spectra of ssDNA-SWCNTs in FIG. 1a presented the population of semiconducting species, while the optical absorption in FIG. 1b showed a fraction of metallic species in the spectral region from 400 to 600 nm. The discrete signatures of the spectra also indicated that the ssDNA-SWCNTs were well dispersed in aqueous solution; otherwise, it would be difficult to see measurable optical transition signatures. The Raman signatures of ssDNA-SWCNTs dispersed in the aqueous solution were probed using resonant Raman spectroscopy with 633 nm laser excitation (FIG. 1c). The Raman spectra included a sharp tangential stretching mode at ~1590 $cm^{-1}$ (G peak) and a broader band around 2600 $cm^{-1}$ (2D peak) of carbon nanotubes.[57] After the deposition of ssDNA-SWCNTs on the electrode, we recorded the visible image of the electrode (FIG. 1d) and the corresponding, raster-scanned Raman image of SWCNTs based on the intensity of G band (FIG. 1e). The Raman image appeared to be similar to the visible image of the electrode, suggesting that nanotubes were well distributed on the electrode. FIG. 1f presented the Raman spectra measured at the two marked positions (#1 and #2) shown in FIG. 1e, where the G and 2D peaks were prominent. In contrast to the solution-phase SWCNTs in FIG. 1c, the Raman spectra of ssDNA-SWCNTs on the electrode showed a discrete D peak or so-called a disorder peak at ~1310 $cm^{-1}$ (FIG. 1f), indicating some defects in SWCNTs. The D peak have been observed in typical deposited nanotubes, and this disclosure shows in the following sections that the defects did not significantly affect the electrochemical activities of SWCNTs for biosensor fabrication and biomolecular detection.

SEM images of micro electrodes modified with different schemes are shown in FIGS. 2a through 2e. Pt black exhibited the typical structure of a film consisting of amorphous clusters of Pt nanoparticles (FIGS. 2a and b), while the layered (FIGS. 2c and d), the co-deposition (FIGS. 2e and f) and the combination schemes (FIGS. 2g and h) show both cluster structure and line structure, indicating that Pt black was growing along ssDNA-SWCNTs. Magnified images (FIGS. 2b, 2d, 2f, and 2h) show that Pt clusters are deposited at defect sites of ssDNA-SWCNTs to form the lines (FIG. 2d) according to previous studies. Compared with the more flat structure of Pt black (FIG. 2b) and co-deposition (FIG. 2f) electrodes, the structure of the layered (FIG. 2d) and the combination (FIG. 2h) electrodes are more three-dimensional with a higher density of Pt nanoparticles, suggesting that the immobilized ssDNA-SWCNTs promoted the three-dimensional growth of Pt black. Since surface expansion of the electrodes was determined by the vertical growth of metal nanomaterials, the more three-dimensional structure should increase the effective surface area and the electro-oxidation of $H_2O_2$, which is the intermediate for glucose and ATP biosensors.

Electrochemical Characterization. Cyclic voltammetry (CV) in $Fe(CN)_6^{3-}$ for the unmodified microelectrodes exhibited typical sigmoid curves with steady state diffusion limited currents (FIG. 3a). The CV data for Pt black electrodes exhibited redox peaks with characteristics of macroelectrodes (FIG. 3a), demonstrating that the surface expansion by Pt black was significant. For the layered electrodes the CV analysis showed even larger redox peak currents than Pt black, indicating a larger effective surface area associated with this surface modification. Peak separation for the layered electrodes did not increase as peak currents increased, suggesting that the incorporation of ssDNA-SWCNT did not affect the electrochemical reversibility of electrodes. Effective surface area for modified electrodes can be quantified from CV data with the Randles-Sevcik equation:

$$i_p = (2.69 \times 10^5) n^{3/2} D^{1/2} C A v^{1/2}$$

where: $i_p$ is the reduction peak current (A), n is the number of transferred electrons for the redox reaction of $Fe(CN)_6^{3-}$, D is the diffusion coefficient ($6.70 \times 10^{-6}$ $cm^2$ $sec^{-1}$), C is the molar concentration of ferricyanide (4 mM), A is the electroactive surface area ($cm^2$), and v is the scan rate (V $sec^{-1}$). After carrying out CV at different scan rates (v=20, 50, 100, 125, 150 and 200 mV/s), effective surface areas of the modified electrodes were determined from the slope of linear regression between $i_p$ and $v^{1/2}$. Histogram for the average effective surface area of micro electrodes based on different schemes was shown in FIG. 3b. Pt black electrodes ($4.7 \times 10^{-4} \pm 1.3 \times 10^{-4}$ $cm^2$) had an average surface area more than ten thousand times that of bare electrodes (specified as $1.8 \times 10^{-8}$ $cm^2$), and the layered electrodes ($2.9 \times 10^{-3} \pm 9.9 \times 10^{-4}$ $cm^2$) showed an even larger surface area compared with Pt black. As previously mentioned, expansion of surface area may be related to the vertical growth of Pt black. This data (FIG. 3b) demonstrated that the use of ssDNA-SWCNT as molecular templates for electrodepositing Pt black can further enhance the expansion of surface area over Pt black. This result is in agreement with SEM images, where the layered electrodes were more three-dimensional than Pt black (FIG. 2d and FIG. 2b). The disclosed histogram data (FIG. 3b) also shows that the surface area of the co-deposition electrodes ($1.9 \times 10^{-4} \pm 6.8 \times 10^{-5}$ $cm^2$) is smaller compared with Pt black ($4.7 \times 10^{-4} \pm 1.3 \times 10^{-4}$ $cm^2$), and that the combination ($1.2 \times 10^{-3} \pm 3.7 \times 10^{-4}$ $cm^2$) is smaller than the layered ($2.9 \times 10^{-3} \pm 9.9 \times 10^{-4}$ $cm^2$). This result suggests that adding ssDNA-SWCNT into the electrodeposition media did not enhance the surface expansion, probably because most of the ssDNA-SWCNTs may have been dispersed in the solution rather than being attached to the electrode surface, so electrical contact is not adequately established between SWCNTs and the electrode. This result indicates that the effective use of ssDNA-SWCNTs as templates for electrodepositing Pt black benefits from the immobilization of ssDNA-SWCNTs (e.g., via cast-and-dry).

Figure 4:
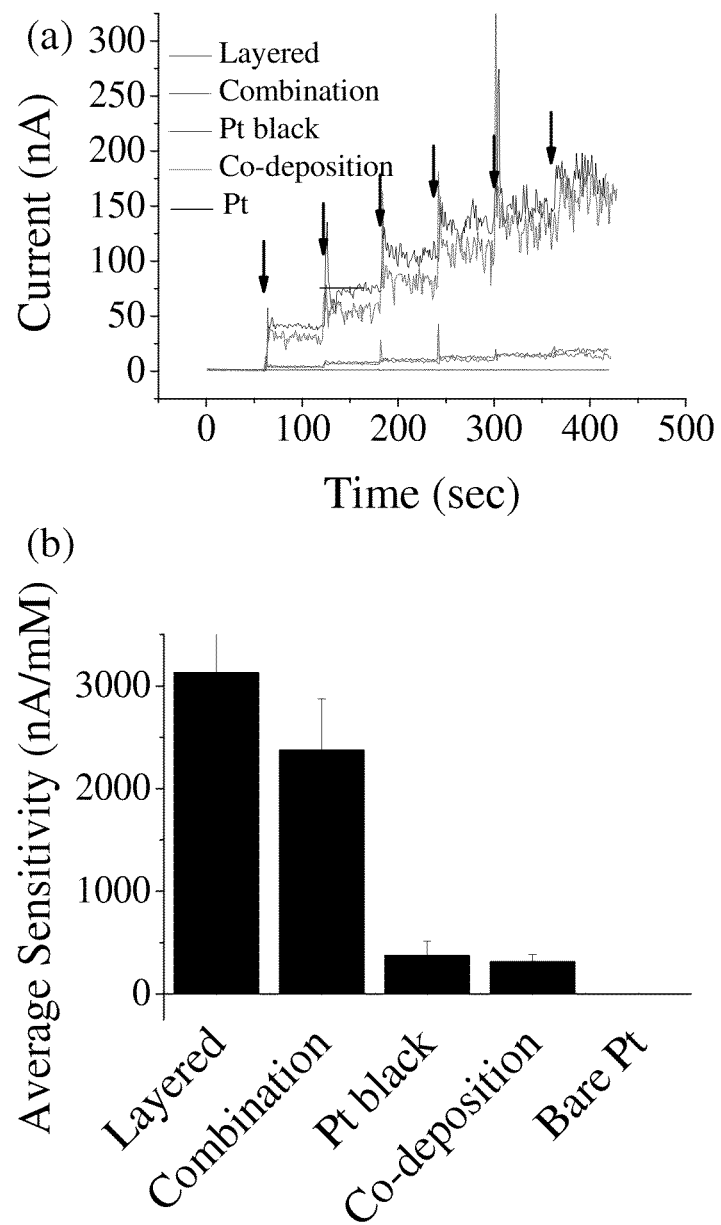
FIG. 4(a) illustrates amperometric response to hydrogen peroxide ($H_2O_2$) for a bare electrode and electrodes modified with Pt black, layered, co-deposition and combination schemes. Arrows represented additions of 10 μM of $H_2O_2$.
FIG. 4(b) illustrates a histogram for the average sensitivity of micro electrodes based on different schemes (error bars represent standard error of the mean (n=3)).

$H_2O_2$ is an electro-oxidative intermediate for enzyme based biosensors. To examine the enhancement in electrocatalytic activities by nanomaterials towards $H_2O_2$ oxidation, DC potential amperometry at +500 mV was carried out for micro electrodes modified with different schemes. All the electrodes showed well-defined amperometric response to $H_2O_2$ (FIG. 4a). For different schemes, a trend similar to surface area was observed (FIG. 4b). The Pt black electrode (375.7±140.1 nA/mM) had a significantly increased $H_2O_2$ sensitivity than the bare electrode (1.3±0.1 nA/mM), and the sensitivity for the layered electrode (3129.9±483.2 nA/mM) was even higher, demonstrating that ssDNA-SWCNT further enhanced the electrocatalytic activities of Pt black. The data also showed (FIG. 4b) that the sensitivity for co-deposition (317.0±68.0 nA/mM) was not significantly different from Pt black (375.7±140.1 nA/mM), and that combination (2375.1±497.2 nA/mM) was not significantly different from layered (3129.9±483.2 nA/mM) ($\alpha$=0.05), indicating that adding ssDNA-SWCNTs to the electrodeposition media did not increase the electrocatalytic activities of Pt black.

Biosensing. Glucose oxidase (GOx), the de facto enzyme, was immobilized on the micro electrodes via the covalent linker glutaraldehyde to construct glucose biosensors. Glucose was electrochemically measured in two steps:

Step 1. GOx converted glucose and $O_2$ into gluconic acid and $H_2O_2$,

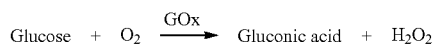
$$\text{Glucose} + O_2 \xrightarrow{\text{GOx}} \text{Gluconic acid} + H_2O_2$$

Step 2. $H_2O_2$ was electrochemically oxidized in the proximity of biosensor at +500 mV,

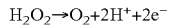
$$H_2O_2 \rightarrow O_2 + 2H^+ + 2e^-$$

Figure 5:
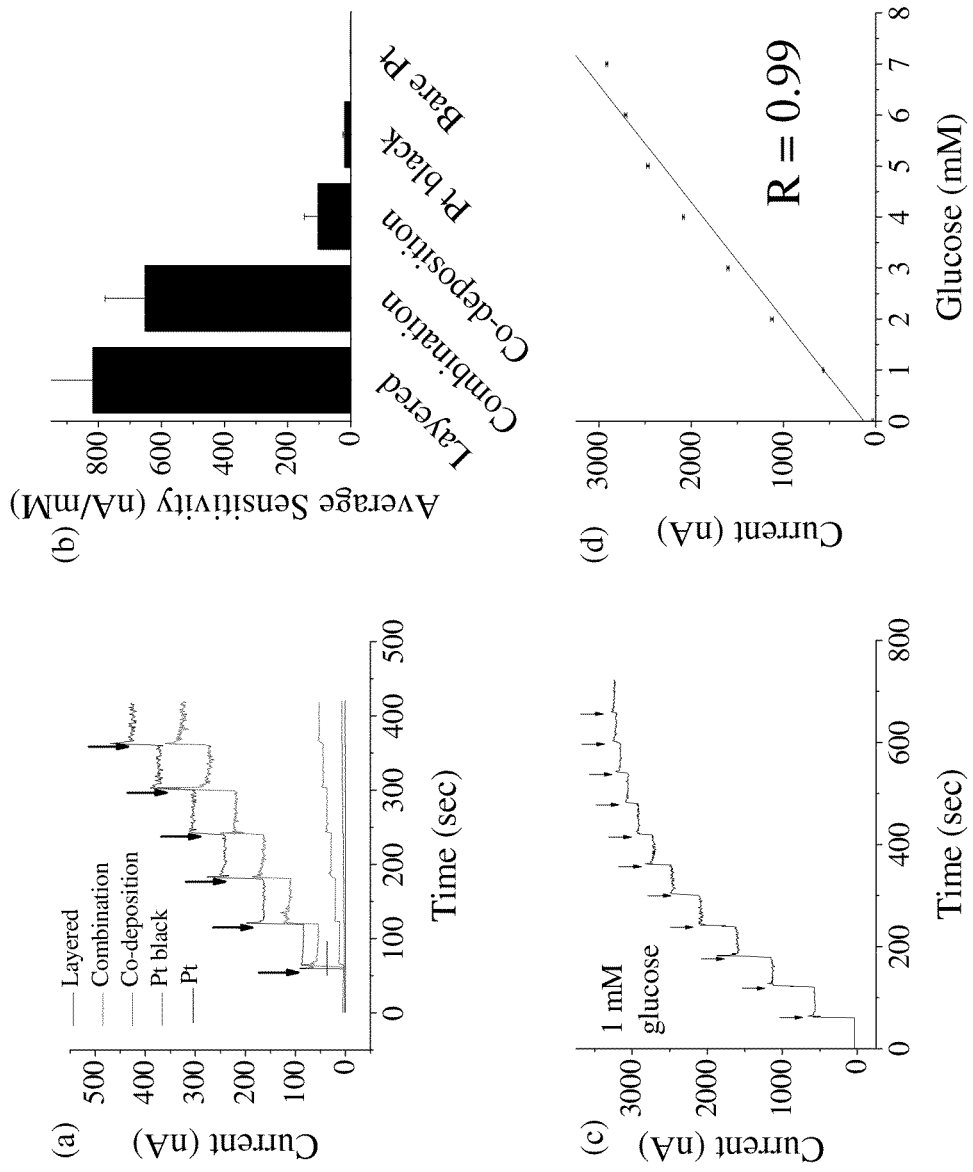
FIG. 5(a) illustrates a representative amperometric response to glucose for a bare electrode and electrodes modified with Pt black, layered, co-deposition and combination schemes. Arrows represented additions of 100 μM glucose.
FIG. 5(b) illustrates a histogram for the average sensitivity of micro electrodes based on the different schemes shown in FIG. 5a (error bars represented standard error of the mean (n=3)).
FIG. 5(c) illustrates a representative amperometric response of a glucose micro biosensor based on layered scheme throughout a linear range.
FIG. 5(d) illustrates the linear regression for the layered scheme of FIG. 5(c).

The measured current was therefore proportional to the glucose concentration. Well-defined amperometric response was observed for biosensors based on each design (including a Pt/GOx biosensor design fabricated by linking GOx to a bare micro electrode) (FIG. 5a). Similar to $H_2O_2$ sensitivity, the Pt black/GOx biosensors possessed significantly increased glucose sensitivity (18.3±5.7 nA/mM) than Pt/GOx biosensors (0.8±0.2 nA/mM) (FIG. 5b). The enhancement was even more significant for the layered biosensors (817.3±185.8 nA/mM) when ssDNA-SWCNT was incorporated as the template for the electrodeposition of Pt black. For the 2 designs (co-deposition and combination) with mixed ssDNA-SWCNT/electro-deposition media, the sensitivity for co-deposition biosensors (102.7±43.9 nA/mM) was higher than Pt black, and that for the combination (651.6±127.1 nA/mM) was lower than the layered. In a word, among all the schemes in this study, results proved the layered approach the most effective for constructing single-enzyme glucose biosensor.

For the layered biosensors, linear response range was up to 7 mM (R=0.99), limit of detection was 1 $\mu$M and response time ($t_{95}$) was ~5 sec (FIGS. 5c&d). The linear range covered the glucose range in normal human blood (~5 mM) and in many cell culture media (e.g., 5.5 mM in mesenchymal stem cell basal medium), demonstrating the wide potential applications of glucose biosensors based on the layered design.

ATP micro biosensors were constructed by attaching the bienzyme system of GK and G3POx to electrodes via glutaraldehyde. ATP was measured in three steps:

Step 1. GK transferred one phosphate from ATP to glycerol,

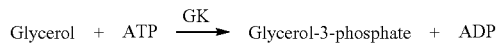
$$\text{Glycerol} + \text{ATP} \xrightarrow{\text{GK}} \text{Glycerol-3-phosphate} + \text{ADP}$$

Step 2. glycerol-3-phosphate was oxidized by G3POx, and $H_2O_2$ was generated,

$$\text{Glycerol-3-phosphate} + O_2 \xrightarrow{\text{G3POx}} \text{Dihydroxyacetone phosphate} + H_2O_2$$

Step 3. The current from oxidizing $H_2O_2$ was measured, as Step 2 in glucose sensing.

Figure 6:
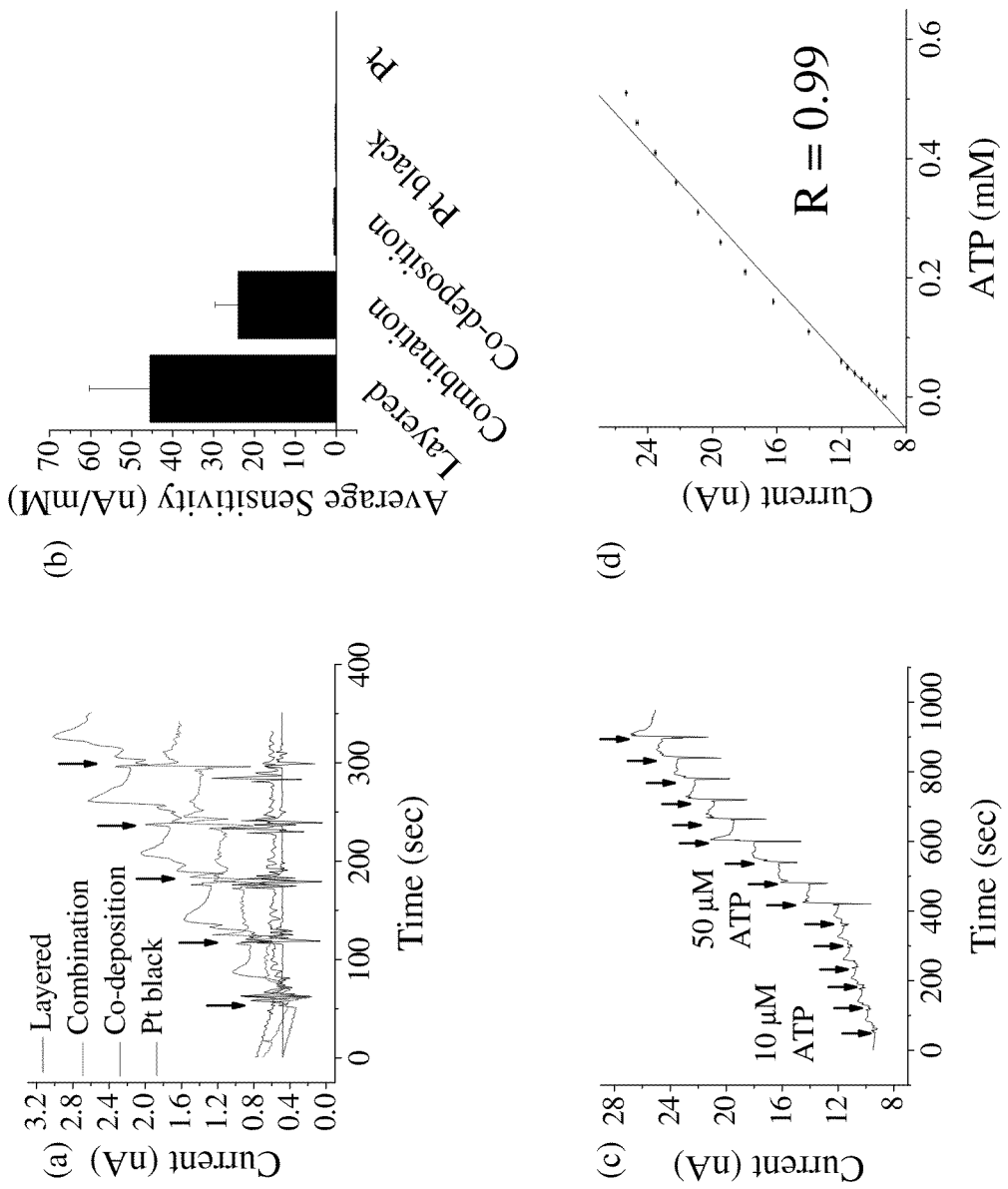
FIG. 6(a) illustrates a representative amperometric response to ATP for electrodes modified with Pt black, layered, co-deposition and combination schemes. Arrows represent additions of 10 μM ATP.
FIG. 6(b) illustrates a histogram for the average sensitivity of micro electrodes based on the different schemes shown in FIG. 6a (error bars represented standard error of the mean (n=3)).
FIG. 6(c) illustrates a representative amperometric response of an ATP micro biosensor based on layered scheme throughout a linear range.
FIG. 6(d) illustrates the linear regression for the layered scheme of FIG. 6(c).

Bare micro electrodes with enzymes attached showed no observable response to ATP, while all the nanomaterial modified electrodes showed well-defined linear amperometric response, demonstrating the great advantage of nanomaterial modified biosensors over biosensors based on conventional materials (FIG. 6a). The sensitivity of biosensors based on the layered scheme (45.6±10.8 nA/mM) was 216 times that of Pt black (0.21±0.08 nA/mM), justifying the effectiveness of incorporating ssDNA-SWCNTs with Pt black. The sensitivity of the co-deposition biosensors (0.57±0.29 nA/mM) was higher than Pt black, and the combination (23.9±5.7 nA/mM) was lower than the layered, although the differences were not significant via ANOVA tests ($\alpha$=0.05) (FIG. 6b). Similar to glucose biosensors, the layered scheme is validated as the most effective for constructing multi-enzyme ATP biosensor. ATP biosensors based on the layered design showed a detection limit of 2 $\mu$M, a linear range up to 510 $\mu$M and a response time of ~8 sec (FIGS. 6c and d). The linear detection range covers human plasma ATP concentration range (up to 11 $\mu$M) and is wider than previous disclosure (up to 50 $\mu$M), suggesting potential applications as physiological sensors. The enhanced performance of the layered scheme exhibited for single-enzyme and multi-enzyme biosensors justified that this scheme was an effective way of combining ssDNA-SWCNT and Pt black, which provided an excellent platform to construct biosensors for a wide variety of physiological applications.

This disclosure explores possible schemes of combining ssDNA-SWCNT and Pt black to enhance enzyme based biosensors. Modification of SWCNTs with ssDNA overcomes the insolubility issue with CNT immobilization, and makes possible the simple aqueous media based approaches for utilizing CNT for biosensing. Optical absorption and photoluminescence profiles demonstrated that ssDNA-SWCNTs were well dispersed in DI water. SEM images and CV analyses showed that the for "layered scheme", where ssDNA-SWCNTs were immobilized on the electrode followed by electrodepositing Pt black, the expansion of effective surface area was more significant compared with Pt black. This is due to nanostructured three-dimensional growth of Pt black by ssDNA-SWCNTs as a template. This result was supported by electrocatalytic activity characterization, where the layered electrodes showed the highest $H_2O_2$ sensitivity (3129.9±483.2 nA/mM) among all schemes. Single-enzyme glucose micro biosensors and multi-enzyme ATP micro biosensors based on the layered design exhibited high sensitivity (817.3±185.8 nA/mM and 45.6±10.8 nA/mM, respectively), wide linear range (up to 7 mM and 510 $\mu$M) and low limit of detection (1 $\mu$M and 2 $\mu$M). For the first time, this disclosure presents a novel ssDNA-SWCNT/Pt black nanocomposite based on the layered scheme that effectively combines the advantages of two important nanomaterials (ssDNA-SWCNT and Pt black). The nanocomposite is an excellent platform for enhancing enzyme based biosensors and holds great promise for versatile sensing applications.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A biosensor comprising,
an electrode including a first layer comprising DNA immobilized with carbon nanotubes on the surface of the electrode and a second layer of Pt black on said first layer.

2. The biosensor of claim 1, further comprising a cross-linking agent.

3. The biosensor of claim 2, wherein the cross-linking agent is glutaraldehyde.

4. The biosensor of claim 3, further comprising an enzyme bound to Pt black by the cross-linking agent.

5. The biosensor of claim 4, wherein the enzyme is selected from the group consisting of glucose oxidase, hexokinase, glycerol kinase, glycerol-3-phosphate oxidase, and any combination thereof.

6. The biosensor of claim 4, wherein the enzyme is glucose oxidase.

7. The biosensor of claim 6, wherein the electrode is configured to measure glucose.

8. The biosensor of claim 4 wherein the enzyme is part of a multi-enzyme combination.

9. The biosensor of claim 8 wherein the multi-enzyme combination includes glucose oxidase, hexokinase, glycerol kinase, or glycerol-3-phosphate oxidase.

10. The biosensor of claim 9, wherein the electrode is configured to measure ATP.

11. The biosensor of claim 1 wherein the carbon nanotubes have a single wall.

12. The biosensor of claim 11 wherein the DNA is single strand DNA.

13. The biosensor of claim 1 wherein the carbon nanotubes are immobilized with DNA prior to the placement of said first layer on the surface.

14. A method of manufacturing a biosensor, the method comprising:
providing an electrode for use with aqueous media;
preparing carbon nanotubes coated with DNA;
coating a surface of the electrode with the DNA-coated carbon nanotubes;
placing Pt black on the coated electrode, and
attaching an enzyme to the coated electrode after said placing the Pt black.

15. The method of claim 14 wherein said coating includes use of a cast and dry method.

16. The method of claim 14, wherein the enzyme is selected from the group consisting of glucose oxidase, hexokinase, glycerol kinase, glycerol-3-phosphate oxidase, and any combination thereof.

17. The method of claim 14 further comprising testing for an analyte selected from the group consisting of glucose and ATP.

18. The method of claim 14 wherein said placing is by electrodeposition.

19. The method of claim 18 wherein the electrodeposition is with a solution containing Pt black and DNA-coated carbon nanotubes.

20. The method of claim 14 wherein said preparing is with single strand DNA and the carbon nanotubes have a single wall.

* * * * *